US008846328B2

(12) United States Patent
Davis et al.

(10) Patent No.: US 8,846,328 B2
(45) Date of Patent: Sep. 30, 2014

(54) METHOD FOR DETECTING THE PRESENCE OF A PROTEASE ENZYME IN A SAMPLE

(71) Applicant: Mologic Limited, Befordshire (GB)

(72) Inventors: Paul J. Davis, Bedfordshire (GB); Mark J. Davis, Bedfordshire (GB); Mark Burnapp, Bedfordshire (GB); Sandra Hemmington, Bedfordshire (GB)

(73) Assignee: Mologic Ltd, Bedfordshire (GB)

( * ) Notice: Subject to any disclaimer, the term of this patent is extended or adjusted under 35 U.S.C. 154(b) by 0 days.

(21) Appl. No.: 13/733,438

(22) Filed: Jan. 3, 2013

(65) Prior Publication Data

US 2013/0189719 A1    Jul. 25, 2013

Related U.S. Application Data

(63) Continuation of application No. 12/280,290, filed as application No. PCT/GB2007/000643 on Feb. 23, 2007, now Pat. No. 8,361,386.

(30) Foreign Application Priority Data

Feb. 23, 2006 (GB) .................................. 0603664.4

(51) Int. Cl.
C12Q 1/37 (2006.01)
(52) U.S. Cl.
USPC ............................................................ 435/23
(58) Field of Classification Search
USPC ........................................ 435/4, 287.7, 287.9
See application file for complete search history.

(56) References Cited

U.S. PATENT DOCUMENTS

| 3,888,629 | A | | 6/1975 | Bagshawe |
| 4,055,394 | A | | 10/1977 | Friedman et al. |
| 4,144,306 | A | * | 3/1979 | Figueras ...................... 422/423 |
| 4,178,153 | A | | 12/1979 | Sodickson |
| 4,258,001 | A | | 3/1981 | Pierce et al. |
| 4,356,149 | A | | 10/1982 | Kitajima et al. |
| 4,522,923 | A | | 6/1985 | Deutsch et al. |
| 4,604,264 | A | | 8/1986 | Rothe et al. |
| 4,689,240 | A | | 8/1987 | Zweig |
| 4,703,017 | A | | 10/1987 | Campbell et al. |
| 4,727,019 | A | | 2/1988 | Valkirs et al. |
| 4,820,489 | A | | 4/1989 | Rothe et al. |
| 4,826,759 | A | | 5/1989 | Guire et al. |
| 4,851,356 | A | | 7/1989 | Canfield et al. |
| 4,870,005 | A | | 9/1989 | Akiyoshi et al. |
| 4,952,520 | A | | 8/1990 | Okusa et al. |
| 5,064,770 | A | | 11/1991 | DeLuca et al. |
| 5,071,746 | A | | 12/1991 | Wilk et al. |
| 5,171,662 | A | | 12/1992 | Sharma |
| 5,185,249 | A | | 2/1993 | Arter et al. |
| 5,236,826 | A | | 8/1993 | Marshall |
| 5,284,622 | A | | 2/1994 | Krause et al. |
| 5,296,192 | A | | 3/1994 | Carroll et al. |
| 5,565,366 | A | | 10/1996 | Akers, Jr. |
| 5,601,986 | A | | 2/1997 | Takacs |
| 5,607,565 | A | | 3/1997 | Azarnia et al. |
| 5,629,164 | A | | 5/1997 | Rivers |
| 5,741,659 | A | | 4/1998 | Ralls et al. |
| 5,755,231 | A | | 5/1998 | Krantz et al. |
| 5,766,961 | A | | 6/1998 | Pawlak et al. |
| 5,879,881 | A | | 3/1999 | Rubenstein |
| 5,932,410 | A | | 8/1999 | Whittaker et al. |
| 5,939,252 | A | * | 8/1999 | Lennon et al. ..................... 435/4 |
| 5,958,790 | A | * | 9/1999 | Cerny ........................... 436/501 |
| 6,040,195 | A | | 3/2000 | Carroll et al. |
| 6,096,563 | A | | 8/2000 | Hajizadeh et al. |
| 6,352,862 | B1 | | 3/2002 | Davis et al. |
| 6,686,170 | B1 | | 2/2004 | Flanders et al. |
| 6,750,034 | B1 | | 6/2004 | Darrow et al. |
| 7,935,497 | B2 | | 5/2011 | Davis et al. |
| 8,241,588 | B2 | | 8/2012 | Davis et al. |
| 8,361,386 | B2 | * | 1/2013 | Davis et al. ................... 422/420 |
| 2003/0207290 | A1 | | 11/2003 | Kenten et al. |
| 2003/0211560 | A1 | | 11/2003 | O'Brien et al. |
| 2003/0219833 | A1 | | 11/2003 | Guan et al. |
| 2004/0029186 | A1 | | 2/2004 | Haworth et al. |
| 2004/0038217 | A1 | | 2/2004 | Yang |
| 2004/0067168 | A1 | | 4/2004 | Buffiere et al. |
| 2004/0096926 | A1 | | 5/2004 | Packard et al. |
| 2005/0164311 | A1 | | 7/2005 | Inglese et al. |

(Continued)

FOREIGN PATENT DOCUMENTS

CA    2569487 A1    12/2005
EP    0339450 A2    11/1989

(Continued)

OTHER PUBLICATIONS

U.S. Appl. No. 13/070,950, filed Mar. 24, 2011, Davis et al.
Anonymous, "Quick-StepTM HCG—One Step Urine Pregnancy Test", Product of Innovative Medical Inc, Internet Citation, XP002423569 (1998).
Secchi et al., "Monoclonal antibody capture fluorometric enzyme linked immunosorbent assay for detection of porcine growth hormone in plasma," Analytica Chimica Acta. 402:37-45 (1999).

(Continued)

Primary Examiner — Ralph Gitomer

(74) Attorney, Agent, or Firm — Clark & Elbing LLP

(57) ABSTRACT

An enzyme detection product for detecting the presence of an enzyme in a sample. The product includes: a reaction zone for receiving the sample; a visualization zone for presenting a signal in response to the detection of the activity of the enzyme; and a membrane. The membrane is interposable between the reaction zone and the visualization zone and prevents passage from the reaction zone to the visualization zone the components having a size greater than a threshold size. The reaction zone includes a reactant capable of reacting with the enzyme in order to generate a reaction product having a size less than a threshold size.

5 Claims, 10 Drawing Sheets

(56) References Cited

U.S. PATENT DOCUMENTS

| | | |
|---|---|---|
| 2006/0003394 A1 | 1/2006 | Song |
| 2006/0234284 A1 | 10/2006 | Yang |
| 2009/0098020 A1 | 4/2009 | Davis et al. |
| 2009/0148406 A1 | 6/2009 | Jezek |
| 2009/0203059 A1 | 8/2009 | Davis et al. |
| 2011/0086370 A1 | 4/2011 | Schouten |
| 2012/0059266 A1 | 3/2012 | Davis et al. |
| 2012/0149032 A1 | 6/2012 | Davis |
| 2013/0053543 A1 | 2/2013 | Davis et al. |

FOREIGN PATENT DOCUMENTS

| | | |
|---|---|---|
| EP | 0206075 B1 | 12/1989 |
| EP | 0158964 B1 | 11/1990 |
| EP | 0450714 A2 | 10/1991 |
| EP | 0579250 A2 | 1/1994 |
| EP | 1394270 A2 | 3/2004 |
| EP | 1986779 A1 | 11/2008 |
| EP | 1989549 A1 | 11/2008 |
| EP | 1991870 A1 | 11/2008 |
| EP | 2004845 A1 | 12/2008 |
| FR | 2621393 A1 | 4/1989 |
| GB | 2259362 A | 3/1993 |
| GB | 2342993 A | 4/2000 |
| GB | 2350677 A | 12/2000 |
| GB | 2410086 A | 7/2005 |
| JP | 57064160 A | 4/1982 |
| JP | 2001000197 A | 1/2001 |
| WO | WO-89/10564 A1 | 11/1989 |
| WO | WO-91/14000 A1 | 9/1991 |
| WO | WO-92/15879 A1 | 9/1992 |
| WO | WO-96/30751 A1 | 10/1996 |
| WO | WO-96/38727 A1 | 12/1996 |
| WO | WO-98/00703 A1 | 1/1998 |
| WO | WO-98/33069 A1 | 7/1998 |
| WO | WO-98/50778 A1 | 11/1998 |
| WO | WO-99/67647 A1 | 12/1999 |
| WO | WO-00/62061 A1 | 10/2000 |
| WO | WO-00/63700 A1 | 10/2000 |
| WO | WO-01/25789 A1 | 4/2001 |
| WO | WO-01/31337 A2 | 5/2001 |
| WO | WO-02/35216 A1 | 5/2002 |
| WO | WO-02/42770 A1 | 5/2002 |
| WO | WO-02/48674 A2 | 6/2002 |
| WO | WO-03/012443 A2 | 2/2003 |
| WO | WO-03/058252 A2 | 7/2003 |
| WO | WO-2004/048935 A3 | 6/2004 |
| WO | WO-2004/103939 A1 | 12/2004 |
| WO | WO-2005/005657 A1 | 1/2005 |
| WO | WO-2005/012558 A1 | 2/2005 |
| WO | WO-2005/119253 A1 | 12/2005 |
| WO | WO-2006/006961 A1 | 1/2006 |
| WO | WO-2007/096637 A1 | 8/2007 |
| WO | WO-2007/096640 A1 | 8/2007 |
| WO | WO-2007/096642 A1 | 8/2007 |
| WO | WO-2007/128980 A1 | 11/2007 |

OTHER PUBLICATIONS

Examination Report for Indian Application No. 2020/MUMNP/2008, dated Jan. 24, 2012 (2 pages).
Examiner's Report for Australian Application No. 2007217119, dated Mar. 17, 2011 (2 pages).
Examiner's Report for Australian Application No. 2007217119, dated Sep. 22, 2011 (2 pages).
International Preliminary Report on Patentability and Written Opinion for International Application No. PCT/GB2007/000641, mailed Sep. 4, 2008 (9 pages).
International Preliminary Report on Patentability and Written Opinion for International Application No. PCT/GB2007/000643, mailed Sep. 4, 2008 (7 pages).
International Preliminary Report on Patentability and Written Opinion for International Application No. PCT/GB2007/001291, mailed Oct. 16, 2008 (6 pages).
International Search Report and Written Opinion for International Application No. PCT/GB2007/000637, mailed May 25, 2007 (8 pages).
International Search Report for International Application No. PCT/GB2007/000641, mailed Jun. 5, 2007 (3 pages).
International Search Report for International Application No. PCT/GB2007/000643, mailed Jun. 1, 2007 (3 pages).
International Search Report for International Application No. PCT/GB2007/001291, mailed Sep. 14, 2007 (2 pages).
Japanese Patent Publication No. 2004-267202, published Sep. 30, 2004, and machine English translation (36 pages).
Office Action for Japanese Application No. 2008-555875, mailed Jun. 28, 2011, and English language translation (6 pages).

* cited by examiner

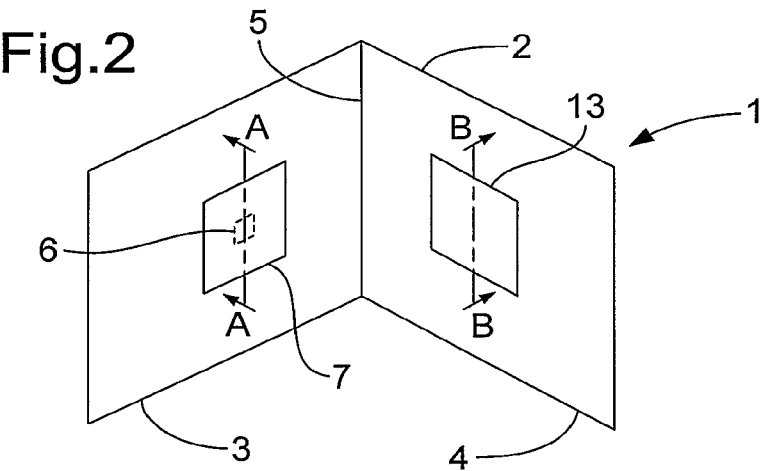
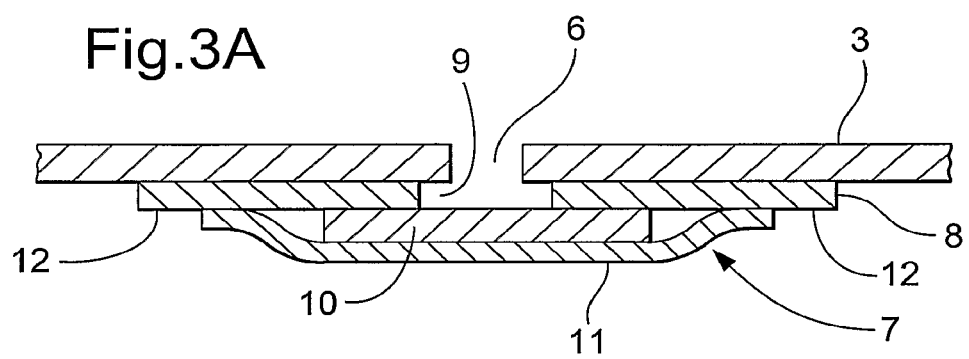
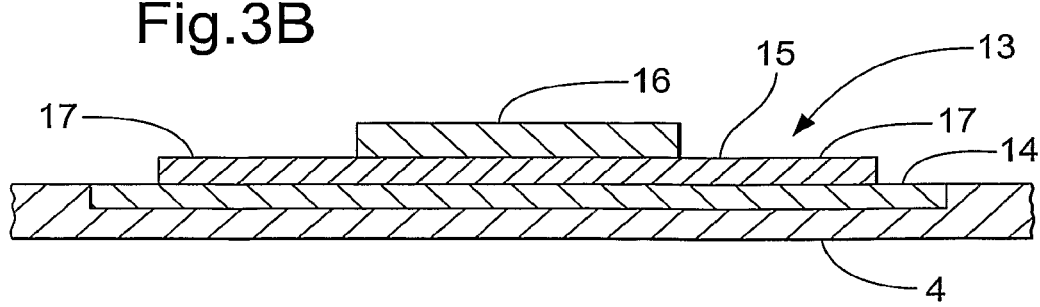

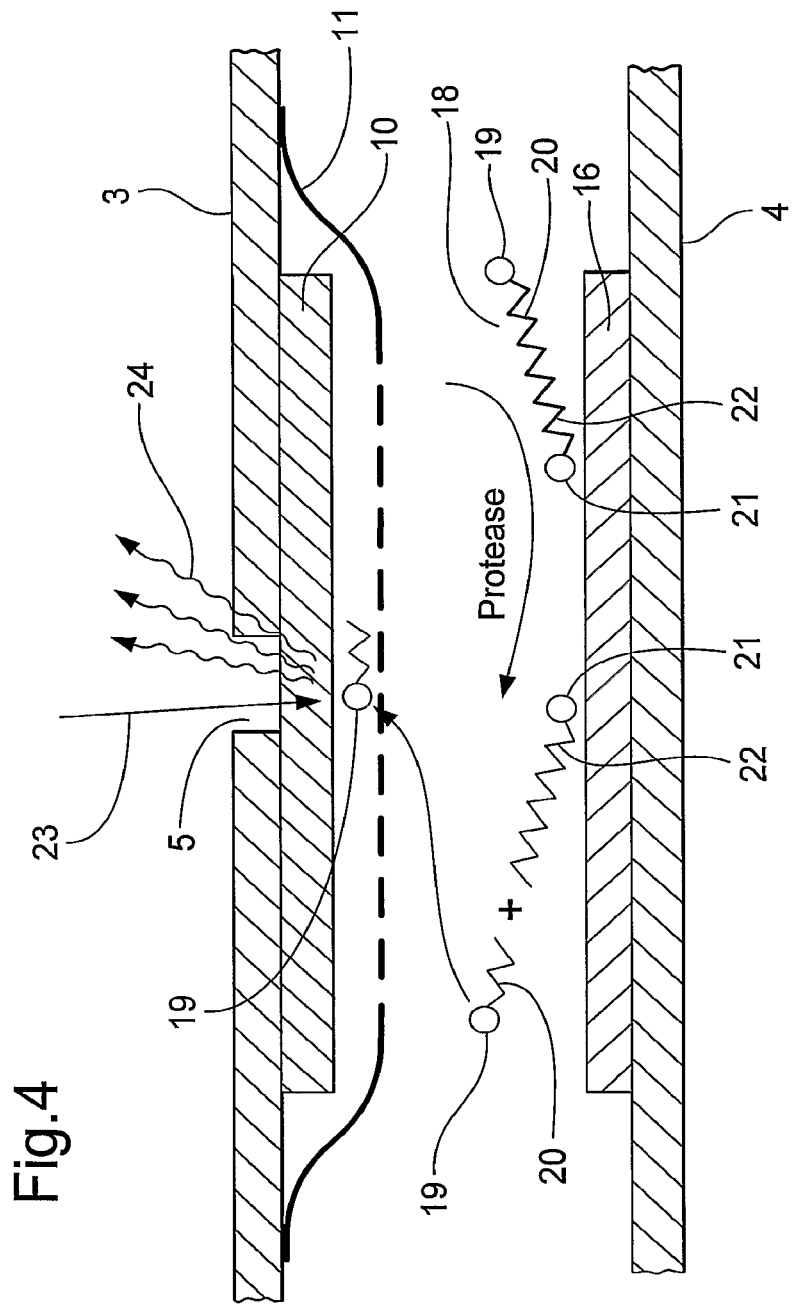

700µgml   350µgml   70µgml   7µgml   0

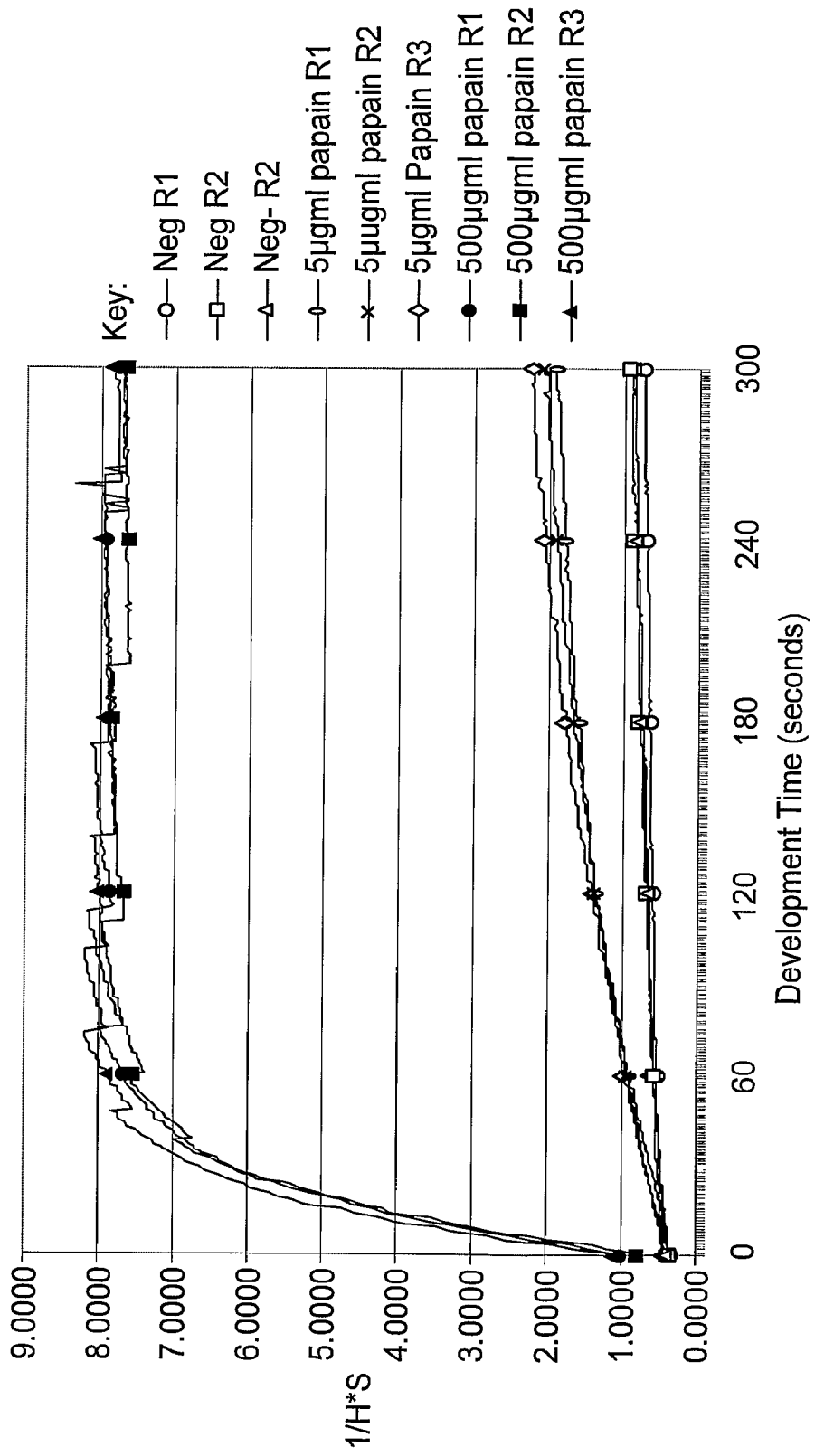

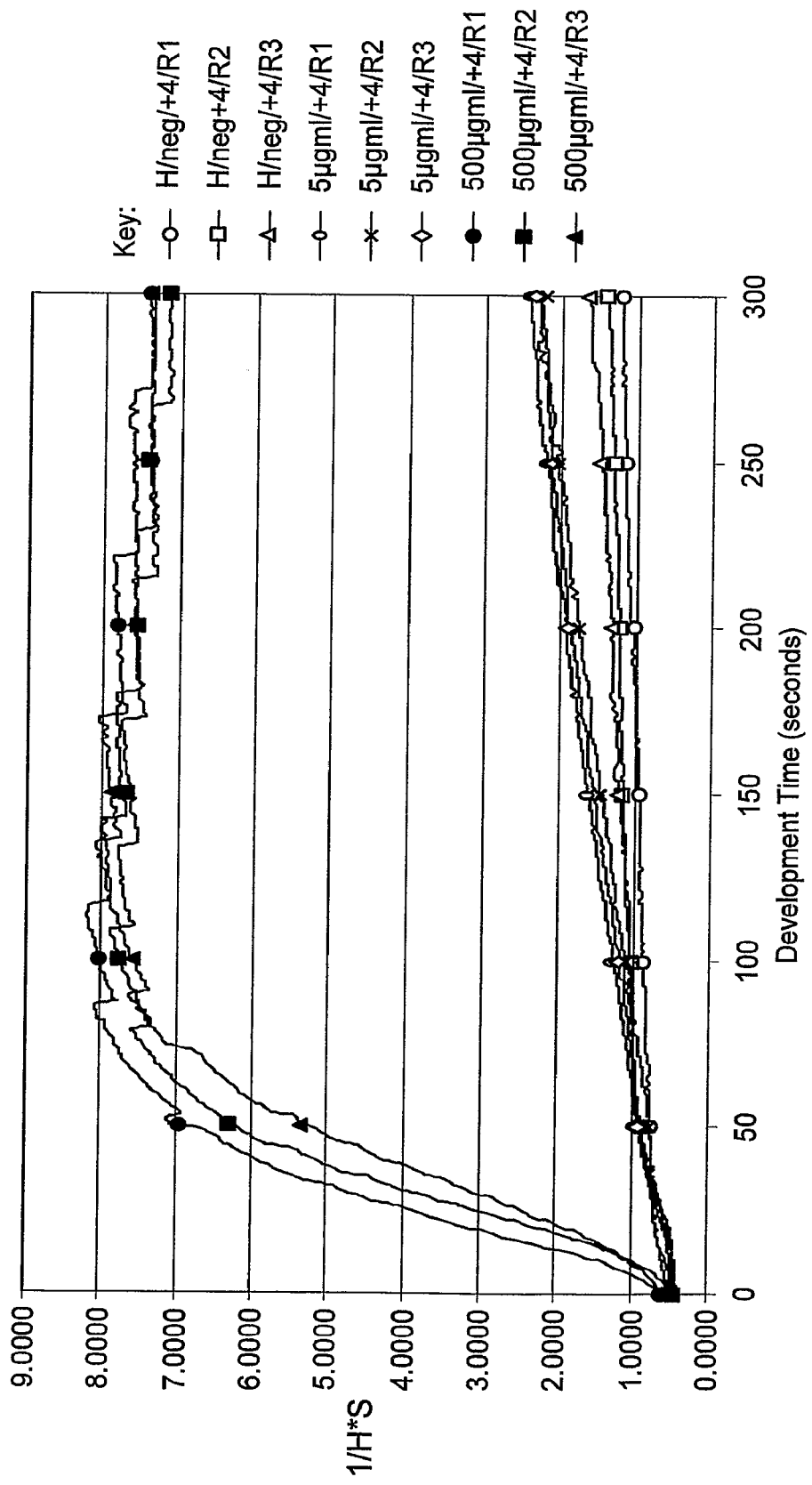

METHOD FOR DETECTING THE PRESENCE OF A PROTEASE ENZYME IN A SAMPLE

This application is a continuation application of Ser. No. 12/280,290 filed Nov. 6, 2008, now U.S. Pat. No. 8,361,386, which is a National Stage application filed under Rule 371 based on PCT/GB2007/000643 filed Feb. 23, 2007.

The present invention relates to an enzyme detection product and also to a method for detecting the presence of an enzyme.

It is known in the art to detect the presence of enzymes under a variety of circumstances. Aside from laboratory methods, kits have been provided which allow the detection of specific enzymes, or types of enzymes without specialist equipment.

For example, it has been disclosed to provide a kit for use by a dentist in order to analyse the gingival crevicular fluid of a patient for the presence of a protease enzyme. A sample of the fluid is taken from the patient and is placed on a filter paper namely loaded with a primary reactant namely the synthetic peptide known as BANA ($N_a$-benzoyl-dl-Arg β-naphthylamide). As is shown in FIG. 1, in the presence of a protease, a naphthylamide moiety is cleaved from the BANA peptide. Another portion of the filter paper is loaded with a secondary reactant DMAC (Dimethyl amino cinnamaldehyde). In response to the presence of the cleaved napthylamine moiety and HCl, DMAC changes colour (from colourless to pink/red). In use, the filter paper is folded over bringing the area loaded with DMAC into contact with the area loaded with BANA and sample, to permit mixing thereof and any colour change is observed. If a colour change occurs then this is an indication that a protease is present in the patient's sample.

While such prior art detection systems work acceptably well, they have several problems in their wider applicability. One problem is that, while gingival crevicular fluid is generally clear, other samples may not be clear and therefore it is more difficult to observe the colour change which may be taking place. For example, if the sample is blood, or contaminated with blood, then it has a strong background colour of its own which may obscure the colour which is produced in the reaction.

Another problem with such prior art systems is that they are susceptible to providing false positive results because the sample, itself, may contain the components which will react with the secondary reactant in order to provide the colour change or other signal. With some chromagenic systems colour may be generated through reactions with amino acids or short peptides (e.g ninhydrin). For instance, to continue the example given above, the gingival crevicular fluid sample may contain a free primary aromatic amine group or an analogue thereof which can react with the DMAC in order to result in a colour change even when no protease is present and the BANA peptide has not been cleaved.

The present invention seeks to alleviate one or more of the above problems.

According to one aspect of the present invention there is provided an enzyme detection product for detecting the presence of an enzyme in a sample comprising:
  a reaction zone for receiving a sample;
  a visualisation zone for presenting a signal in response to the detection of the activity of the enzyme, wherein the reaction zone comprises a reactant capable of reacting with the enzyme in order to generate a reaction product. The reaction zone is pre-treated with the reactant.

Preferably, the product further comprises a membrane interposable between the reaction zone and the visualisation zone, the membrane preventing passage from the reaction zone to the visualisation zone of components having a size greater than a threshold size and wherein the reaction product has a size less than the threshold size.

The membrane has a molecular weight threshold. This is preferably of less than 100 kDa, 50 kDa, 10 kDa, 5 kDa, 1 kDa or 500 Da.

Conveniently, the membrane is opaque.

Preferably, the reaction zone and/or the visualisation zone comprise films made of an absorbent material which hydrates but does not dissolve in the presence of water.

Advantageously, the film is made from PVA, pectin, acrylamide, agarose, pululan or a carrageenan.

Conveniently, the visualisation zone is made from a material which allows uniform colour development.

Preferably, the reaction zone and the visualisation zone are hingedly connected to each other and may be brought into contact with each other by flexing about the hinge.

Advantageously, at least one of the reaction zone and visualisation zone has an adhesive area extending around its perimeter for sealingly contacting the reaction zone with the visualisation zone.

Conveniently, the visualisation zone is mounted on a leaf, there being provided an aperture in the leaf, for viewing of the visualisation zone.

Preferably, the aperture is covered by a transparent window.

Advantageously, the reaction zone has a sump made from an absorbent material located adjacent to it.

Preferably, a layer is located between the reaction zone and the sump, such as an adhesive layer. It is particularly preferred that the layer extends laterally outwardly of the reaction zone. For example, if the reaction zone and the layer are circular then the layer has a greater diameter than the reaction zone.

Conveniently, at least one of the reaction zone and visualisation zone is covered by a removable protective film.

Preferably, the visualisation zone comprises a second reactant capable of reacting with the reaction product to generate the signal.

Advantageously, the enzyme is a protease; the first reactant being the BANA peptide and the second reactant being D-MAC.

Conveniently, the enzyme detection product further comprises a sample dispersion means for facilitating the lateral movement of the sample; breaking up the surface of the reaction zone and forming channels therein to conduct the sample therethrough.

According to another aspect of the present invention, there is provided a method of detecting the presence of an enzyme in a sample comprising the steps of:
  i) contacting the sample with a first reactant, the reactant producing a reaction product in the presence of the enzyme;
  ii) separating at least some of the components in the mixture which are smaller than a threshold size into a visualisation zone, the reaction product being smaller than the threshold size; and
  iii) detecting the presence of the reaction product in the visualisation zone.

Conveniently, step ii) comprises using a selective membrane to separate components in the mixture.

Preferably, step ii) comprises observing the reaction product or a signal released by the reaction product.

Advantageously, step i) is carried out on a reaction substrate and step iii) is carried out on a visualisation substrate.

Conveniently, the method further comprises the step of, after step i), contacting the reaction substrate with the visualisation substrate.

Preferably, step iii) comprises providing a second reactant, which reacts with the reaction product to generate a signal.

Advantageously, the method uses an enzyme detection product of the invention.

In order that the present invention may be more readily described and so that further features of the invention may be understood, embodiments of the invention shall now be described by way of example, with reference to the accompanying drawings in which:

FIG. 2 is a perspective view of an enzyme detection product in accordance with one embodiment of the invention;

FIG. 3A is a cross-sectional view along the line A-A of the enzyme detection product shown in FIG. 2; and FIG. 3B is a cross-sectional view of the enzyme detection product of FIG. 2 along the line B-B;

FIG. 4 is a schematic cross-sectional view of an enzyme detection product according to an alternative embodiment;

FIG. 9 is graph showing colour development of an enzyme detection product according to another embodiment;

FIG. 10 is graph showing colour development of an enzyme detection product according to another embodiment;

Figure 1:
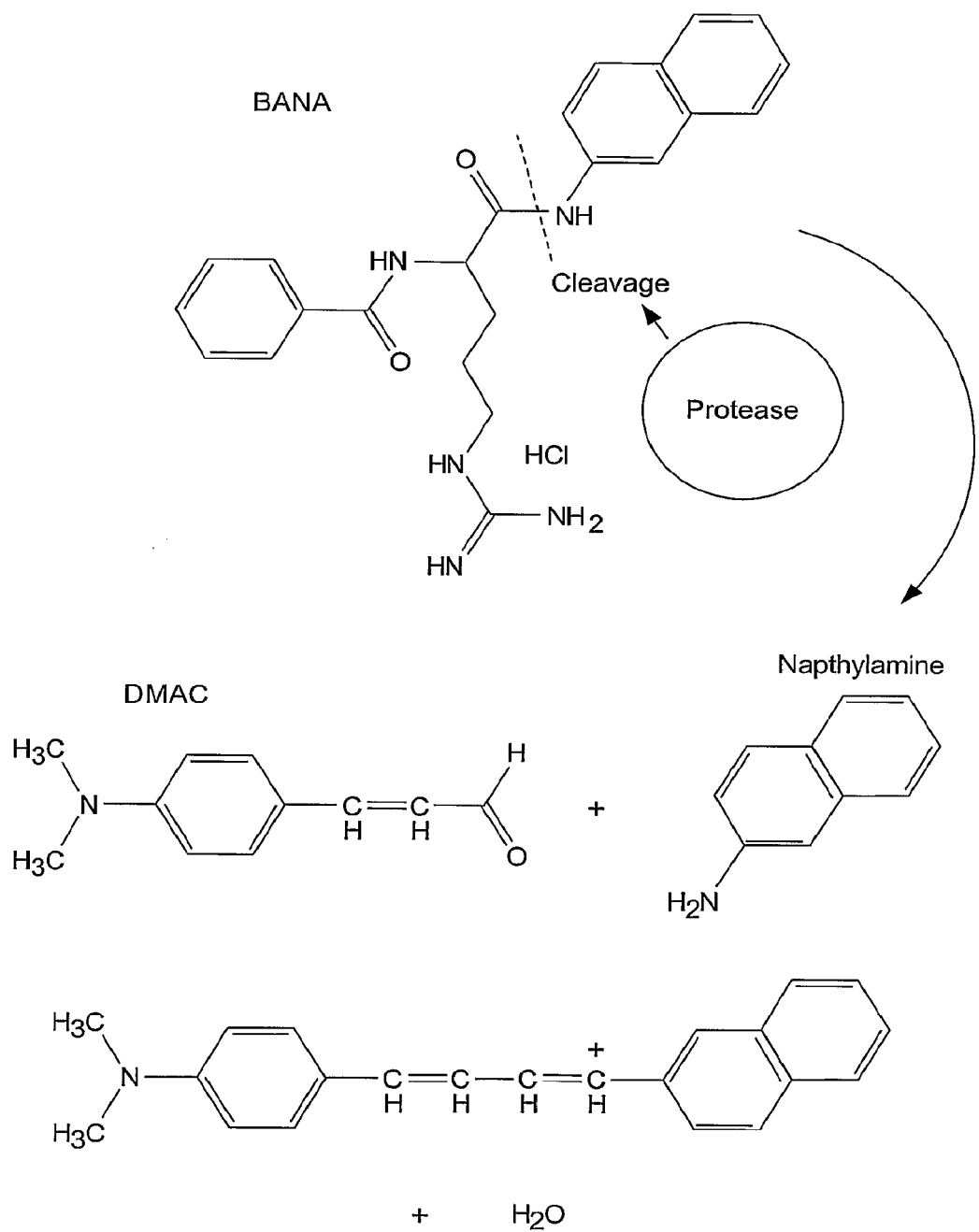
FIG. 1 is a schematic diagram of the reaction of a protease enzyme, BANA and DMAC.

Referring to FIG. 2, an enzyme detection product 1 comprises a paper or cardboard book 2 comprising first and second leaves 3,4 of identical shape and size connected at a spine 5. Thus the spine 5 acts as a hinge between the first and second leaves 3, 4.

In the centre of the first leaf 3, there is provided a first aperture 6 in the book 2. On top of the first leaf 3, covering the aperture 6 is provided a visualisation pad 7 which is covered by a protective film prior to use (not shown).

Referring now to FIG. 3A, the visualisation pad 7 will be described in greater detail. The internal face of the first leaf 3 carries a first adhesive film 8, in which there is an aperture 9 aligned with, but larger than, the first aperture 6. On top of the first adhesive film 8 is provided a visualisation film 10 made from polyvinyl alcohol (PVA) which hydrates but does not dissolve in the presence of water. The visualisation film 10 contains DMAC and HCl within its structure. The visualisation film 10, though centred on the aperture 6, is smaller than the first adhesive film 8. The visualisation film 10 is optically clear, carries no inherent colour and allows uniform colour development. It is non-porous before use.

On top of the visualisation film 10 is provided a membrane 11, which is bigger than the film 10 and thus overlaps the visualisation film 10 and connects at its edges onto the first adhesive film 8. Nonetheless, the membrane 11 is smaller than the first adhesive film 8 so that the edges 12 of the first adhesive film 8 extend outwardly from the membrane 11. The membrane 11 is opaque and is preferably white in colour. It contains a plurality of pores (not shown). The pores render the membrane selective of the molecules which may pass through it. More specifically, molecules having a molecular weight of above a threshold size of 500 daltons cannot pass through the membrane 11, but molecules having a molecular weight of less than 500 daltons may pass through the membrane. In alternative embodiments, the threshold size is greater than 500 Da and may, for example be 1 kDa or 5 kDa.

The second leaf 4 has a reaction pad 13 located in its centre. The reaction pad 13 is located on the second leaf 4 facing the visualisation pad 7 of the first leaf 3. Covering the reaction zone 13 is a removable foil wrapper (not shown). Referring now to FIG. 3B, the reaction pad 13 will be described in further detail.

The reaction pad 13 comprises, attached to the second leaf 4, a second adhesive film 14. On top of the adhesive film 14 (although of a smaller size than the adhesive film 14) is provided an absorbent sump 15. On top of the absorbent pad 15 is provided a reaction film 16 made from polyvinyl alcohol (PVA) and having impregnated into it the synthetic peptide BANA and a sample dispersion material. The sample dispersion material is a fabric which facilitates the lateral movement of the sample on the reaction film 16 by breaking up the surface of the reaction film 16 and forming channels in it through which the sample can be conducted. The reaction film 16 is of the same size as the visualisation film 10 and is thus smaller than the absorbent sump 15 such that the edges 17 of the second adhesive film 14 extend outwardly of the reaction film 16.

In order to use the enzyme detection product 1, the book 2 is opened to separate the first and second leaves 3,4 and the protective films (not shown) covering the visualisation pad 7 and the reaction pad 13 are removed. The sample to be tested (e.g. blood) is deposited on the reaction film 16. Any run-off from the sample is absorbed by the sump 15. The first and second leaves 3,4 of the book 2 are pressed together after an appropriate reaction time (e.g. 60 seconds), such that the edges 12 of the first adhesive film 8 meet the edges 17 of the second adhesive film 14 and cause adhesion between the first and second leaves 3,4. The adhesion of the first and second leaves 3,4 to each other seals the sample within the book 2, which thus hygienically contains the sample.

It is to be noted that, as soon as the sample is placed upon the reaction film 16, any protease enzyme active in the sample will begin hydrolysing the BANA peptide and releasing the napthylamine moiety even before the leaves 3,4 are brought together. The napthylamine moiety is small enough to pass through the membrane 11 and onto the reaction film 10. Other components of the sample which have a molecular weight bigger than the threshold size of 500 daltons are unable to pass through the membrane 11.

When the napthylamine moiety reaches the visualisation film 10, the DMAC and napthylamine condense and change colour to red/pink (see FIG. 1). The visualisation film 10 is visible through the first and second apertures 6,9 in the first leaf 3 and the first adhesive film 8 and thus an observer may see the colour change that takes place. Because the membrane 11 is preferably white in colour, opaque and forms a background to the visualisation film 10, it assists an observer in making an unbiased assessment of the colour change, regardless of sample-derived interfering colour. The colour change is indicative of the presence of a protease enzyme in the sample. The degree of colour change (hue, saturation and absorbance) and the rate of colour change (although not necessarily both) are dependent on the enzyme concentration in the sample and reaction time.

In a sample without protease activity, the napthylamine moiety is not released from the reaction film 16, so when the two leaves 3,4 of the book 1 are brought into contact, the DMAC compound reacts with HCl present in the visualisation film 10 in the presence of the fluid sample to produce a yellow coloured product.

In an alternative embodiment of the invention, a transparent slide or window is attached to the first leaf 3, covering the first aperture 6, on the opposite side of the first leaf 3 from the first adhesive film 8. The transparent slide permits viewing of the visualisation film 10, but does not permit ingress of contaminants or egress of the sample.

In alternative embodiments, the reaction film 16 and the visualisation film 10 are instead made from other materials which hydrate but do not dissolve in water such as acrylamide, agarose, pululan or carrageenans.

It is to be understood that the present invention is not limited to embodiments in which the reaction film 16 is impregnated with BANA peptide and the visualisation film 10 is impregnated with DMAC. Instead, a different set of reactants may be provided on the reaction film 16 and the visualisation film 10, respectively.

For example, DMAC can also be replaced with Fast Garnet (a zinc stabilised diazonium salt) or Fast Black.

Alternatively, the napthylamide group of BANA can be attached to any amino acid sequence of choice to enable detection of particular proteases. For example in order to test for the presence of the enzyme neutophil elastase BANA is replaced with H-DL-Ala-bNA (Bachem).

Reactants can be designed and synthesised for the detection of the presence of the activity of a particular protease enzyme using napthylamide or napthylamide ester labels.

In alternative embodiments, the reactant casein is provided on the reaction film instead of BANA and the reactant ninhydrin is provided on the visualisation film instead of DMAC.

Indeed, it is not essential to the invention that any reactant is provided on the visualisation film 10. For example, referring to FIG. 4, another embodiment is shown schematically. In FIG. 4, like components have the same numbering as in the previous embodiments. Thus, in this embodiment the first and second leaves 3, 4 have a visualisation film 10 covered by a selective membrane 11 and a reaction film 16, respectively. An aperture 6 is provided in the first leaf 3, above the visualisation film 10. The reaction film 16 is impregnated with a cleavable peptide 18 having a fluorophore group 19 covalently attached to one end 20 thereof and a quencher group 21 attached to the other end 22 of the peptide. The peptide 18 is sensitive to a protease enzyme, in that a protease enzyme will cleave the peptide 18 separating the first end 20 to which the fluorophore group 19 is conjugated from the search end 22 to which the quencher group 21 is conjugated. The cleaved first end 20 is small enough to pass through the membrane 11, away from the quencher 23 located on the remaining peptide 18, and into the visualisation film 10, where, under incident light 23 it may be observed to fluoresce visible light 24. However in the absence of the protease in the sample, the peptide is not cleaved and the uncleaved peptide 18 is too big to pass through the membrane 11. Thus in this embodiment, the visualisation film 10 does not contain a component which reacts with any other component and instead acts as a receptacle and viewing area for the reaction product (i.e. the fluorophore group 21 bound to the first end 20).

An example of a suitable fluorophore group is Mca (7-methoxycoumarin-4-acetyl) and a suitable quencher is Dpa (2,4-Dinitrophenyl). Mca, when not in proximity to Dpa, can be detected fluorometrically at 392 nm (excitation 325 nm).

In an alternative embodiment, the reactant in the reaction film 16 is a peptide, the carboxy end of which is linked via an amide bond to a p-Nitroanilide group. If the peptide is cleaved by a protease enzyme then this releases a p-nitroaniline group which passes through the membrane 11 and is visible as it is yellow in colour.

In another embodiment, BANA is provided on the reaction film 16 but no DMAC is provided in the visualisation film 10. In the presence of a protease enzyme, napthylamine is released and is visible in the visualisation film under UV light. In a further embodiment, the reactant provided on the reaction film 16 is DL arginine amino methyl L coumarin which also releases a fluorescent cleavage product in the presence of a protease enzyme.

It is also to be understood that the present invention is not limited to products for the detection of a protease enzyme. In other embodiments, reactants are provided on the reaction film 16 and, optionally also the visualisation film 10, which are responsive to other enzymes in a sample. For example, in one embodiment amylase is detected by the release of glucose from amylose in the reaction film 16. In this embodiment the visualisation film 10 contains glucose oxidase and an appropriate chromogen, of a type widely known by those skilled in the art.

EXAMPLES

Example 1

Elastase Substrate in a Booklet Format

Materials (Film Preparation)
    H-Ala-Beta-napthylamide (H-Ala-βNA)
    50 mM tris buffer pH 8
    10% Brij 35 in deionised water
    5% PVA in deionised water
    Dimethylaminocinnamaldehyde (DMAC)
    Cotton gauze
    Dimethyl sulfoxide (DMSO)
    3M HCL
    Methanol (MEOH)
    Petri dishes 20 cm
    Deionised water Materials (Device Assembly and Enzyme Assay)
    Cartridge paper
    Double sided adhesive tape
    DMAC film
    H-Ala-βNA film
    Porcine pancreatic elastase
    Small colourimeter (FIG. 6) connected to PC Method (Film Preparation)

H-Ala-βNA film was prepared as follows; discs of gauze were cut to fit inside the base of a standard 18 cm microbiological Petri dish. Further, 20 mgs of H-Ala-βNA was weighed out and added to a universal bottle with 1 ml of DMSO to dissolve. The following reagents were added to the dissolved substrate; 1.5 mls of tris buffer, 100 μl of Brij 35 and 7.5 mls of 5% PVA. The tube was gently inverted to facilitate mixing of the components before pouring the suspension into the Petri dish to cover the gauze. The open dish was placed in a fume hood to dry at ambient temperature for approximately 20 hours.

DMAC films were prepared as follows; 15 mgs of DMAC weighed out and added to a universal with 1.5 mls of MeOH to dissolve. 3.75 mls of HCL was added followed by 2.25 mls of deionised water and 7.5 mls of 5% PVA. The components were mixed by inverting the tube prior to pouring into a clean empty Petri dish. The film was dried at ambient temperature for approximately 20 hours in a fume hood.

Method (Device Assembly)

The cartridge paper was cut into rectangles of approximately 10×5 cm, these were folded in half and the centre point was marked with a pencil on the front cover. A circular punch was used to cut a aperture approximately 12 mm diameter in the front cover of the booklets. The hole was then used to mark the central location on the inside of the opposing leaf of the construction.

Pieces of double sided tape were applied to the inner left and right hand sides.

Film (described above) was cut with circular punches; the H-Ala-βNA was cut with the 12 mm diameter punch and applied to the inner right hand side sticky tape to give the sample application area. DMAC film was cut with a slightly larger punch approximately 15 mm diameter and secured on the double sided tape on the inner left hand side to cover the aperture.

Enzyme Assay

Porcine pancreatic elastase (Sigma) was prepared to give approximately 20 mg/ml in Tris buffer pH 8.

Two devices were run, an enzyme negative sample was applied to device 1 and elastase positive sample was applied to second device. The devices were run consecutively by applying 40 µl of sample to the substrate pad (H-Ala-βNA) and incubating for 10 minutes at room temperature. After the incubation period the device was closed so that the DMAC film contacted the substrate pad and remained closed by the double sided tape.

Figure 5:
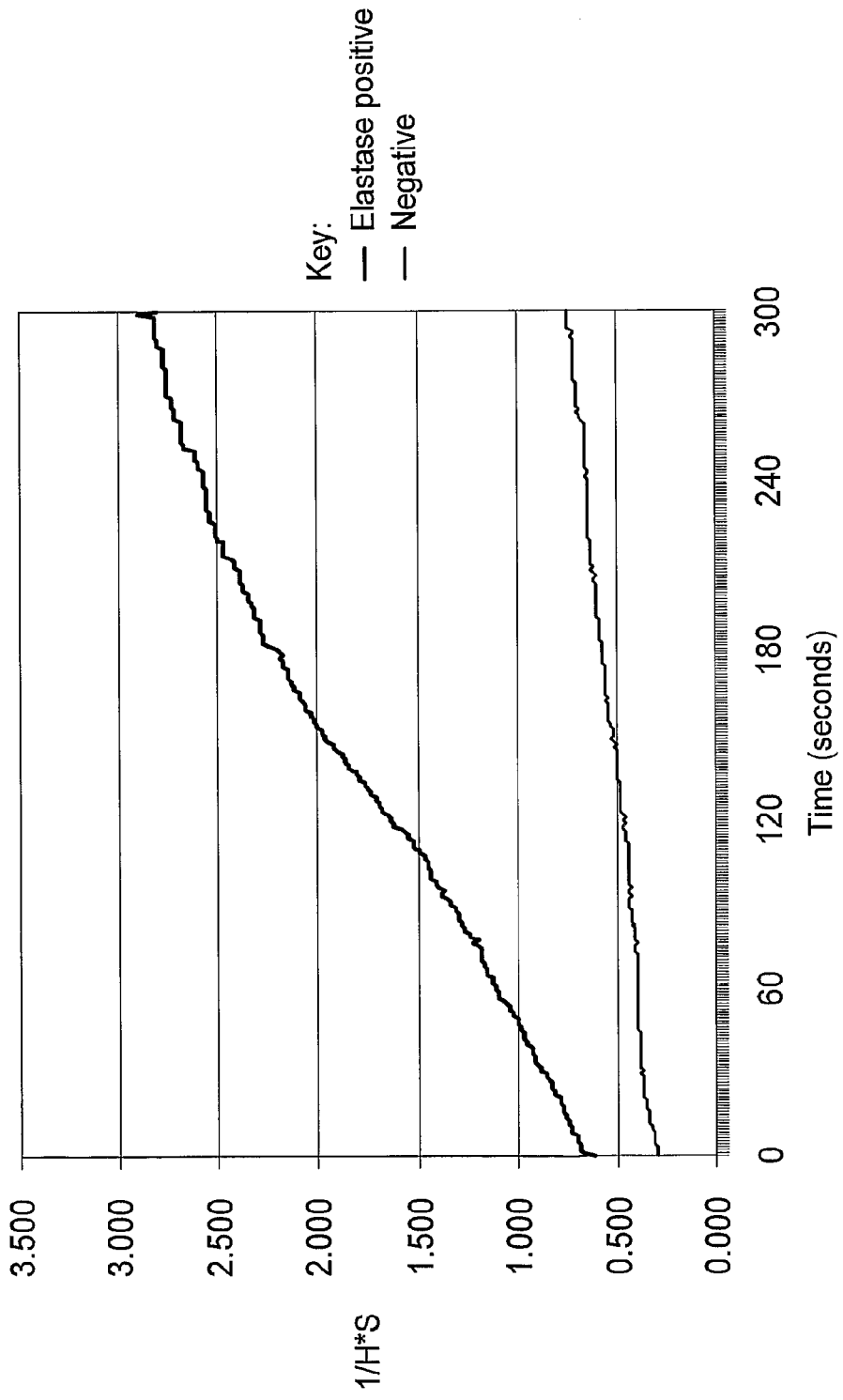
FIG. 5 is a graph showing colour development of an enzyme detection product according to one embodiment.

The colour development was monitored by placing the device viewing window down onto a basic colourimeter. Readings were taken once per second over a total of 5 minutes. The resulting data was compared for Hue (H) and Saturation (S) by using the following equation: 1/H×S. Data can be seen in FIG. 5. Stronger colours generated from a device treated with a positive sample (blue line) have a lower numerical value of H and often greater saturation i.e. S value. Negative samples therefore have a lower flatter trend than positive samples (pink line).

Figure 6:
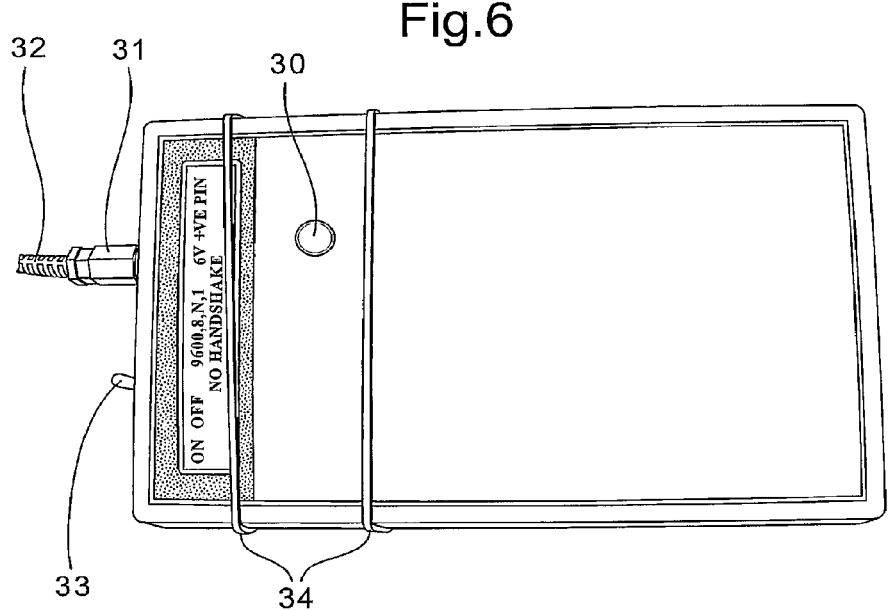
FIG. 6 is a plan view of a colourimeter used in the test whose results are shown in FIG. 5.

The colourimeter is shown in FIG. 6. It consists of a white LED light source and colour sensing chip as detector in a black plastic case to remove ambient light. Components or the colourimeter are as follows: opening for reading devices with white LED 30; power supply 31; connection to computer 32; on/off switch 33; and elastic bands to hold devices in place 34. Raw data is converted by embedded software to give Hue (H), Saturation (S) and Intensity (V) values as well as Red (R), Green (G) and Blue (B) to a terminal emulator application. The readings from the device are based on the colour wheel principle.

Example 2

Fluorescent Label Detection Following Enzymatic Cleavage of Substrate

A. Detection of βNA as a Fluorophore.

Materials
  5% PVA in deionised water
  Cotton gauze
  Dimethyl sulfoxide (DMSO)
  Petri dishes 20 cm
  Deionised water
  250 mM phosphate 25 mM EDTA pH 7.2
  Benzoyl Arginine beta napthylamide. HCL (BANA)
  Petri dish
  Cartridge paper
  Double sided sticky tape Method.

BANA films were prepared as per the H-Ala-βNA film, but with subtle changes.

Discs of cotton gauze were cut to fit the inside of a standard 18 cm microbiological petri dish. 20 mg of BANA were added to a universal and dissolved in 1 ml of DMSO. The following reagents were added; 1 ml of phosphate/EDTA buffer 0.5 ml of deionised water and 7.5 mls of 5% PVA. The suspension was mixed gently and then poured onto the gauze and placed in a fume hood to dry at ambient temperature for approximately 20 hours.

Testing

A piece of cartridge paper approximately 12×5 cm was prepared with small 5 small holes (approximately 5 mm diameter). The holes were each covered with a small square of double sided tape. BANA film was cut to fit the tape on the holes and applied. Prepared papain enzyme standards at 700, 350, 70, 7 µgml in a deionised water with 0.01% cysteine, diluent. A negative of diluent only was also used. The enzyme and control samples were applied at 20 µl per BANA film and incubated at room temperature. The progress of fluorescence development was checked at approximately 5 minute intervals on a UV light box. The results after approximately 14 minutes are given in FIG. 7 and are tabulated in Table 1.

TABLE 1

Figure 7:
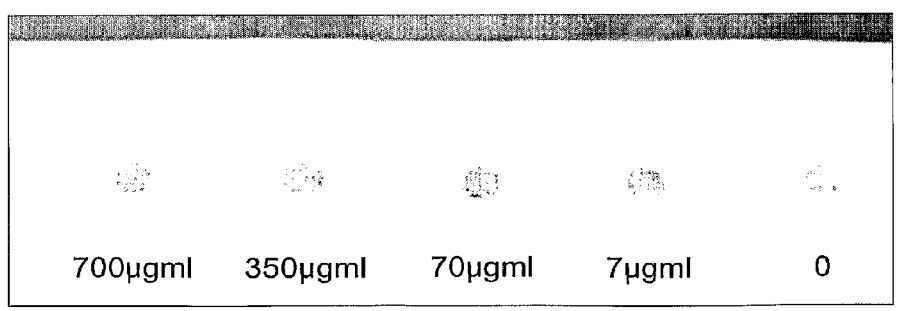
FIG. 7 is an image of an enzyme detection product according to another embodiment, following usage.

Interpretation of fluorescent signal in FIG. 7. (Fluorescent brightness is scored according to the negative.)

| 700 µgml Enzyme | 350 µgml Enzyme | 70 µgml Enzyme | 7 µgml Enzyme | 0 Enzyme |
|---|---|---|---|---|
| ++ | + | − | − | − |

Fluorescence was detected above the background in films that were incubated with 350 and 700 µgml of papain.

B. Detection of Cleaved Bz-DL-Arg-Amino MethylCoumarin.HCL

Materials
  Bz-DL-Arg_AMC.HCL (Bachem 1-1076)
  5% PVA in deionised water
  Cotton gauze
  Dimethyl sulfoxide (DMSO)
  Petri dishes 20 cm
  Deionised water
  250 mM phosphate 25 mM EDTA pH 7.2
  Petri dish
  Cartridge paper
  Double sided sticky tape Method A film was prepared as described in 'A' with the following exception; 10 mg of Bz-DL-Arg_AMC.HCL was added to the DMSO instead of BANA.

Testing

Set up of the test device as previously described in 'A' with the following exception; three rows of 4 pieces of film were attached over the viewing windows instead of 1 row of 5.

Applied fresh papain standards at the following concentrations, 10000, 1000, 100 µgml and 0. Monitoring of the signal generation was as previous. The results are shown in FIG. 8 and are tabulated in Table 2.

TABLE 2

Figure 8:
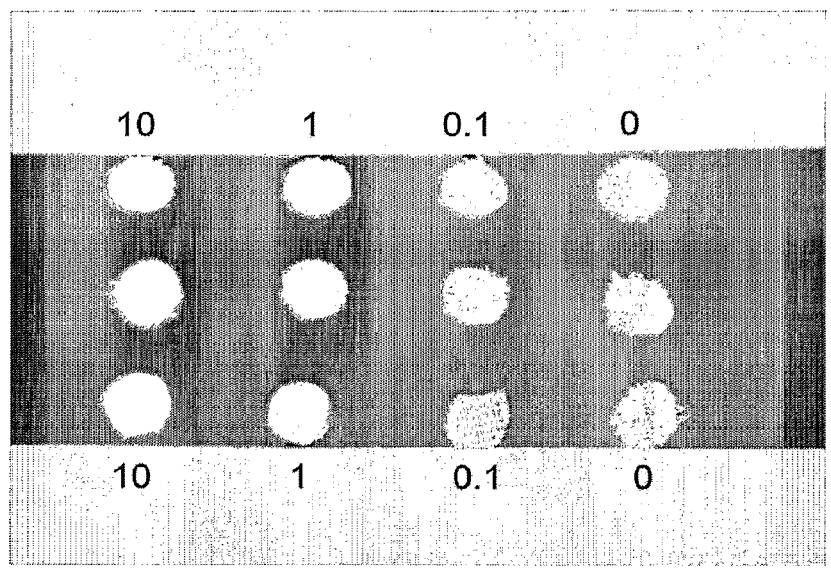
FIG. 8 is an image of an enzyme detection product according to another embodiment, following usage.

Interpretation of fluorescent signal in FIG. 8 (Fluorescent brightness is scored according to the negative).

| 10000 µgml Enzyme | 1000 µgml Enzyme | 100 µgml Enzyme | 0 Enzyme |
|---|---|---|---|
| +++ | ++ | + | − |

Fluorescence was detected at all levels of the enzyme tested.

Example 3

Exemplification of BANA/DMAC Protease Assay Using Storage Data

Preparation of BANA and DMAC Films.
The standard procedures are as follows:
Materials
  Close weave cotton gauze
  5% PVA in deionised water
  Dimethyl sulfoxide (DMSO)
  Petri dishes 20 cm
  Deionised water
  250 mM phosphate 25 mM EDTA pH 7.2
  Benzoyl Arginine beta napthylamide. HCL (BANA)
  Petri dish
  3M HCL
  Methanol (MEOH)
  DMAC
BANA/PVA/Gauze Film
  1) A disc of cotton gauze was cut to fit the inside of a 20 cm Petri dish.
  2) 20 mgs of BANA wad added to a clean universal and dissolved in 1 ml of DMSO.
  3) The following were added to the BANA stock prepare in (2), 1 ml of phosphate/EDTA buffer, 0.5 mls of deionised water and 7.5 mls of 5% PVA.
  4) The solution was mixed gently and then poured onto the gauze and placed in a fume hood to dry for approximately 20 hours.
DMAC/PVA Film
  1) 15 mgs of DMAC was weighed out and added to a clean universal with 1.5 mls of MeOH to dissolve.
  2) The following were added to the DMAC stock prepared in (1), 3.75 mls of HCL was added followed by 2.25 mls of deionised water and 7.5 mls of 5% PVA.
  3) The components were mixed by inverting to tube prior to pouring into a clean empty Petri dish. The film was dried for approximately 20 hours in a fume hood.
Preparation of Papain Standards
  1) A stock solution is prepared freshly each day when required to give 10 mgml enzyme in deionised water with 0.1% cysteine. This stock solution is then used to prepare working strength standards by further dilution in deionised water.
Preparation of Booklet Devices
  1) Booklets prepared from cartridge paper folded to give a booklet of approximately 5×5 cm.
  2) In the centre of the front cover a 12 cm diameter hole (viewing window 6) was punched.
  3) Two pieces of double sided tape of approximately 25 mm square were pieced in the centre of both inside leaves of the booklet as adhesive films 8 and 14.
  4) A 12 mm diameter disc of BANA/PVA/Gauze film 16 was placed in the centre of the adhesive film 14 to be the sample application area.
  5) A 15 mm diameter disc of DMAC/PVA film 10 was placed in the centre of the adhesive film 8 covering the viewing window 6.

Enzyme Assay
Devices materials were prepared and assembled according to our standard methodologies described above. On day 0 (defined as the day materials were dry and ready for device assembly) devices were run to give day 0 results against which stored materials could be compared. Solutions containing papain at concentrations of 500 and 5 µgml and a negative of the diluent only (50 µl volumes per test) were applied to devices for an incubation period of 10 minutes. The booklets were closed and the colour development was monitored using the Mologic booklet device colourimeter which measures the following parameters at 1 second intervals, Hue (H) Saturation (S) Brightness (V) Redness (R) Greenness (G) and Blueness (B).

Devices were stored at 4° C. without a dessicant and assayed over the following 28 days with data for day 0 and day 28 listed below.

Data Manipulation
The colorimeter output measurement data for Hue and saturation were manipulated using the following equation: 1/H×S. The data are shown in FIGS. 9 and 10. FIG. 9 shows a graph showing replicate data for the papain standards tested on day 0 devices. FIG. 10 shows a graph showing replicate data for papain standards tested on day 28.

Table 3 compares the calculated slopes and readings at certain time points.

TABLE 3

|  | Negative | 5 µg ml Papain | 500 µg ml Papain |
|---|---|---|---|
| Slope Day 0 | 0.003 | 0.00865 | 0.103 |
| Slope Day 28 | 0.007 | 0.010 | 0.107 |
| Av.1/H * S day 0 |  |  |  |
| 60 seconds | 0.569 | 0.921 | 7.731 |
| 90 seconds | 0.614 | 1.149 | 7.917 |
| 120 seconds | 0.649 | 1.364 | 8.00 |
| Av.1/H * S day 28 |  |  |  |
| 60 seconds | 0.897 | 0.876 | 6.745 |
| 90 seconds | 0.956 | 1.093 | 7.580 |
| 120 seconds | 1.028 | 1.288 | 7.828 |

The data illustrates a reduced rate of signal development in the day 28 positive samples. However, the comparison of the averaged data shows little significant change in the final signal values, in the case of positive samples this is achieved in a slightly longer time frame.

Example 4

Evaluation of Selective Membranes into Booklet Assay

Using the standard BANA/DMAC format booklet (as described in Example 3) the following 'selective' membranes have been incorporated into the device according to FIG. 3A except that the visualisation window 6 was completely sealed with the adhesive film 8 such that here is no aperture 9 to minimise evaporation during substrate incubation.

A wide range of membranes evaluated in Protease Booklet ranging from a 0.22 µm pore size filters to a MWCO 3500 Da dialysis membrane as listed below.
  Millipore Isopore membrane—0.1 µm, 25 µm thick VCTP
  Millipore MF membrane—0.2 µm, 150 µm thick GSPW Millipore Durapore membrane—0.22 µm, 150 µm thick GV Whatman Nylon membrane—0.2 µm pore, 150 µm thick Degussa ceramic composite membranes—type S240 P25—25 µm thick Dialysis membranes—Pierce Snakeskin prod #68035, MWCO 3,500 and Spectra/Por cat #132723, MWCO 3,500

Amicon NMWL membrane—cat #PBCC 04310, NMWL 5,000

Booklets were prepared with each of the membranes as described above and then tested with 0, 50 and 250 µg/ml Papain standards using sample volumes of 40 µl for the control devices and 80 µl for devices incorporating the membrane to ensure sufficient liquid added to the device to wet all booklet components. Standards were added to the BANA film and incubated for 10 minutes. The booklets were then closed and colour development recorded by capturing digital images over a 30 minute period.

Figure 11:
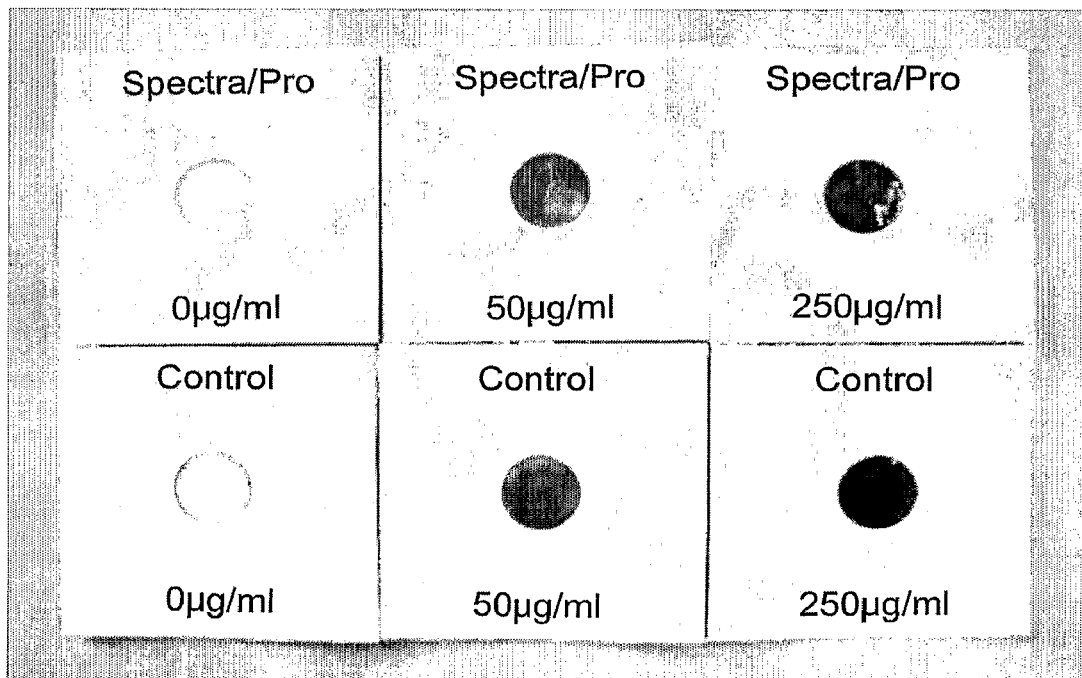
FIG. 11 is an image of an enzyme detection product according to another embodiment, following usage.

FIG. 11 shows digital images of booklets without a selective membrane (control booklets) and with a MWCO 3,500 dialysis membrane following 15 minute incubation. The results are tabulated in Table 4.

TABLE 4

Signal Generation for Booklets incorporating Selective Membranes

| Papain Standard | Control Booklet | Membrane Booklet |
|---|---|---|
| 0 µg/ml | − | − |
| 50 µg/ml | + | + |
| 250 µg/ml | +++ | +++ |

Example 5

Evaluation of a Sink in the Booklet

Figure 12:
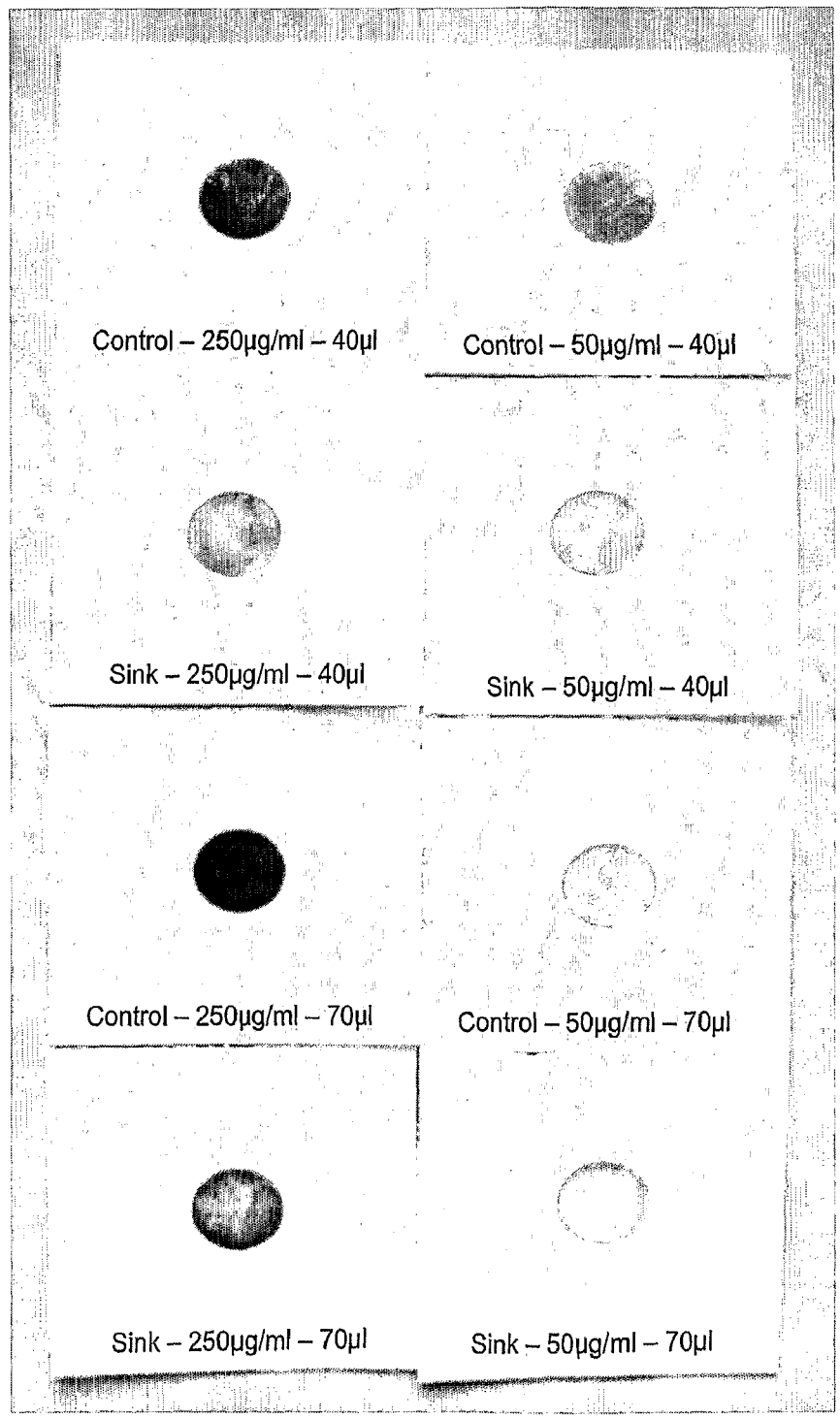
FIG. 12 is an image of an enzyme detection product according to another embodiment, following usage.

Various sink formats were tested in the booklet type protease where in all cases the sink was larger than and placed beneath the BANA film which was held onto the sink using double sided tape. Two materials were tested, Fisherbrand QL 100 filter paper and Bibby Sterilin Bench Guard with the second material having a much greater absorbancy and void volume.

Where the double sided tape is of the same diameter or smaller then the BANA film (12 mm diameter or less)—as in FIG. 3B—then it was seen that the 'sample' wicked from the sample pad into the sink via the gauze fibres or directly through the PVA film such that the BANA film would be nearly dry after the initial sample incubation which led to uneven and poor signal generation. FIG. 12 is a digital image of booklets according to FIG. 3B with and without a sink using 40 and 70 µl sample volume showing effect of liquid removal from Sample Pad and Reduced Signal. The results are tabulated in Table 5.

TABLE 5

Signal Generation for Booklets incorporating sink according to FIG. 3B

| Papain Standard | Sample Volume 40 µl | | Sample Volume 70 µl | |
|---|---|---|---|---|
| | Control | Sink | Control | Sink |
| 50 µg/ml | ++ | + | + | +/− |
| 250 µg/ml | ++++ | ++ | ++++ | ++ |

Figure 13:
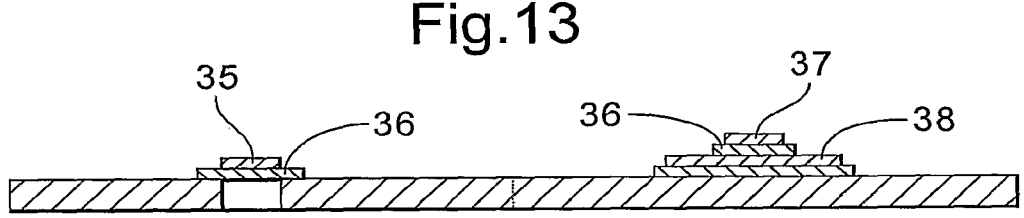
FIG. 13 is a cross-sectional diagram of an enzyme detection product according to a further embodiment.
Figure 14:
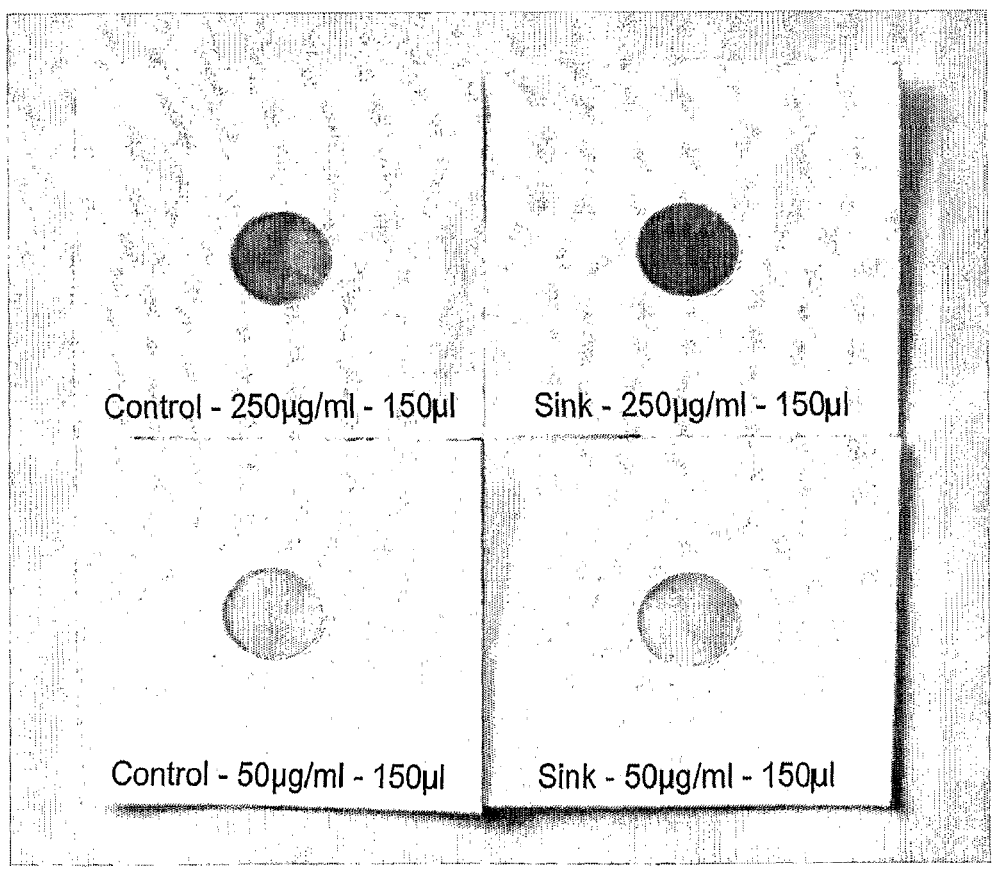
FIG. 14 is an image of an enzyme detection product according to another embodiment, following usage.

When the double sided tape was larger than the BANA film such that there was a minimum of 1 mm excess around the whole BANA film (as shown below) it was found that device coped with sample volumes from 40 to ~200 µl of sample without excess not being mopped up by the sink. A diagram of such an embodiment is shown in FIG. 13. Components of FIG. 13 are as follows: DMAC/PVA Film 35; Double Sided Tape 36; BANA/PVA/Gauze Film 37; and sink/sump 38. A digital image of booklets with and without sink tested using 150 µl sample volume is shown in FIG. 14. The results are tabulated in Table 6.

TABLE 6

Signal Generation for Booklets incorporating sink as shown in FIG. 13

| Papain Standard | Control | Sink |
|---|---|---|
| 50 µg/ml | + | + |
| 250 µg/ml | +++ | +++ |

The invention claimed is:

1. A method of detecting the presence of a protease in a sample comprising the steps of:
   i) contacting the sample with a first reactant, the reactant being a peptide capable of being cleaved by the protease and producing a reaction product in the presence of the protease, wherein said reaction product is detectable as a consequence of cleavage by the protease;
   ii) separating at least some of the components in the sample which are smaller than a threshold size into a visualisation zone, the reaction product being smaller than the threshold size; wherein said separating comprises using a selective membrane interposed between the reaction zone and visualization zone to separate components in the sample, the membrane preventing passage from the reaction zone to the visualization zone of components having a greater size than the threshold size; and
   iii) detecting the presence of the reaction product in the visualisation zone in order to indicate the presence of the protease in the sample.

2. A method according to claim 1 wherein step ii) further comprises observing the reaction product or a signal released by the reaction product.

3. A method according to claim 1 wherein step i) is carried out on a reaction substrate and step iii) is carried out on a visualisation substrate.

4. A method according to claim 3 and further comprising the step of, after step i), contacting the reaction substrate with the visualisation substrate.

5. A method according to claim 1 wherein step iii) further comprises providing a second reactant, which reacts with the reaction product to generate a signal in order to indicate the presence of the protease in the sample.

* * * * *